US012220216B2

(12) United States Patent
Chen et al.

(10) Patent No.: US 12,220,216 B2
(45) Date of Patent: *Feb. 11, 2025

(54) NON-CONTACT EXERCISE VITAL SIGN DETECTION METHOD AND EXERCISE VITAL SIGN DETECTION RADAR

(71) Applicant: Wistron Corporation, New Taipei (TW)

(72) Inventors: Jye-Hong Chen, New Taipei (TW); King-Leong Li, New Taipei (TW); Yin-Yu Chen, New Taipei (TW); Kai-Jen Cheng, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 523 days.

This patent is subject to a terminal disclaimer.

(21) Appl. No.: 17/678,362

(22) Filed: Feb. 23, 2022

(65) Prior Publication Data

US 2023/0138670 A1 May 4, 2023

(30) Foreign Application Priority Data

Oct. 29, 2021 (TW) .................................. 110140489

(51) Int. Cl.
*A61B 5/05* (2021.01)
*A61B 5/00* (2006.01)
(Continued)

(52) U.S. Cl.
CPC .............. *A61B 5/05* (2013.01); *A61B 5/7257* (2013.01); *A61B 5/7264* (2013.01);
(Continued)

(58) Field of Classification Search
None
See application file for complete search history.

(56) References Cited

U.S. PATENT DOCUMENTS 10,374,863 B2 8/2019 Xu et al.
10,576,328 B2 3/2020 Santra et al.
(Continued)

FOREIGN PATENT DOCUMENTS

CN 109188414 A 1/2019
CN 109740522 A 5/2019
(Continued)

OTHER PUBLICATIONS

Examination report dated Jun. 23, 2022, listed in related Taiwan patent application No. 110140492.
(Continued)

*Primary Examiner* — Patricia J Park
(74) *Attorney, Agent, or Firm* — McClure, Qualey & Rodack, LLP (57) ABSTRACT

A non-contact exercise vital sign detection method is provided. At least one candidate position having an energy intensity exceeding an energy threshold is pre-selected from a vibration frequency map, and a position having a vibration frequency meeting a vital sign parameter range is then selected as a target position from the at least one candidate position. Accordingly, phase data obtained according to the target position facilitates accurate detection of a vital sign parameter of a subject.

22 Claims, 9 Drawing Sheets

(51) Int. Cl.
  *G01S 7/35* (2006.01)
  *G01S 7/41* (2006.01)
(52) U.S. Cl.
  CPC ............ *A61B 5/7275* (2013.01); *G01S 7/354* (2013.01); *G01S 7/356* (2021.05); *G01S 7/412* (2013.01)

(56) References Cited

U.S. PATENT DOCUMENTS

| | | |
|---|---|---|
| 10,617,330 B1 | 4/2020 | Joshi et al. |
| 2019/0007256 A1 | 1/2019 | Chen et al. |
| 2019/0104954 A1 | 4/2019 | Campbell et al. |
| 2019/0142289 A1 | 5/2019 | Bliss et al. |
| 2019/0212429 A1 | 7/2019 | Yamanouchi |
| 2019/0212436 A1 | 7/2019 | Baheti et al. |
| 2019/0216393 A1 | 7/2019 | Baheti et al. |
| 2020/0041610 A1 | 2/2020 | Longman et al. |
| 2020/0103516 A1 | 4/2020 | Kim et al. |
| 2020/0116824 A1 | 4/2020 | Yang et al. |
| 2020/0155038 A1 | 5/2020 | Katabi et al. |
| 2020/0180472 A1 | 6/2020 | Lu-Dac et al. |
| 2020/0191913 A1 | 6/2020 | Zhang et al. |
| 2021/0045651 A1 | 2/2021 | Li et al. |
| 2021/0093203 A1 | 4/2021 | Zhong et al. |
| 2021/0109208 A1* | 4/2021 | Horng ................. A61B 5/7225 |
| 2021/0197834 A1 | 7/2021 | Shaker et al. |
| 2024/0264272 A1* | 8/2024 | Kiuru ..................... G01S 13/42 |

FOREIGN PATENT DOCUMENTS

| | | |
|---|---|---|
| CN | 110450784 A | 11/2019 |
| CN | 110946555 A | 4/2020 |
| CN | 110946587 A | 4/2020 |
| CN | 106821347 B | 5/2020 |
| CN | 111142102 A | 5/2020 |
| CN | 111812633 A | 10/2020 |
| CN | 112263242 A | 1/2021 |
| CN | 112386237 A | 2/2021 |
| CN | 112560803 A | 3/2021 |
| CN | 113281739 A | 8/2021 |
| CN | 114647009 A | 6/2022 |
| DK | 202070213 A1 | 12/2021 |
| EP | 2428814 A1 | 3/2012 |
| EP | 3 901 651 A1 | 10/2021 |
| KR | 20180089427 A | 8/2018 |
| WO | 2018031516 A1 | 2/2018 |
| WO | 2018183546 A1 | 10/2018 |
| WO | 2018206934 A1 | 11/2018 |
| WO | 2019070651 A1 | 4/2019 |
| WO | 2019079855 A1 | 5/2019 |
| WO | 2019122412 A1 | 6/2019 |
| WO | 2019122413 A1 | 6/2019 |
| WO | 2019144413 A1 | 8/2019 |
| WO | 2020102813 A1 | 5/2020 |
| WO | 2020104465 A2 | 5/2020 |

OTHER PUBLICATIONS

Examination report dated Apr. 11, 2022, listed in related Taiwan patent application No. 110140489.
Exercise Vital Signs Detection Employing FMCW Radar and Artificial Neural Networks; 2020.
Music-based algorithm for range-azimuth FMCW radar data processing without estimating number of targets; 2015.
Extended European Search Report dated Oct. 10, 2022, listed in related European patent application No. 22 172 256.4.
Examination report dated May 8, 2024, listed in related U.S. Appl. No. 17/678,492 (Publication No. US 2023-0138670A1).
Takuya Sakamoto, etc., " Noncontact Measurement of the Instantaneous Heart Rate in a Multi-Person Scenario Using X-Band Array Radar and Adaptive Array Processing", IEEE Journal on Emerging and Selected Topics and Systems, vol. 8, No. 2, IEEE, Jun. 2018 Abstract, Figure 1, Papers I., IV, VI, VII.
Examination report dated Jan. 15, 2024, listed in related Taiwan patent application No. 110140492.

* cited by examiner

NON-CONTACT EXERCISE VITAL SIGN DETECTION METHOD AND EXERCISE VITAL SIGN DETECTION RADAR

CROSS-REFERENCE TO RELATED APPLICATION

This non-provisional application claims priority under 35 U.S.C. § 119(a) to Patent Application No. 110140489 filed in Taiwan, R.O.C. on Oct. 29, 2021, the entire contents of which are hereby incorporated by reference.

BACKGROUND

Technical Field

The present invention relates to radar technologies, and in particular, to a non-contact exercise vital sign detection method and an exercise vital sign detection radar.

Related Art

There are many wearable or direct-contact vital sign parameter measurement devices that can monitor vital sign parameters (such as a heart rate) in activities of daily living. However, wearing a wearable or contact device for a long time makes a subject feel uncomfortable. Although there are still non-contact measurement manners, when the subject is in an exercise state, the shaking of the body of the subject is apt to interfere with measurement, to affect the accuracy of the measurement.

SUMMARY

In view of this, according to some embodiments, a non-contact exercise vital sign detection method is provided, performed by a processor in a signal processing apparatus, the method including: obtaining a digital signal; obtaining a phase map and a vibration frequency map according to the digital signal, where the phase map presents an energy distribution with a distance change relative to an exercise vital sign detection radar and a phase change, and the vibration frequency map presents an energy distribution with the distance change relative to the exercise vital sign detection radar and a vibration frequency change; selecting at least one candidate position having an energy intensity exceeding an energy threshold from the vibration frequency map; selecting a target position from the at least one candidate position, where the target position is a position having a vibration frequency meeting a vital sign parameter range in the at least one candidate position; obtaining one or more pieces of target phase data in a distance range in the phase map according to the target position; and inputting the one or more pieces of target phase data into a machine learning model to obtain a vital sign parameter prediction result.

According to some embodiments, an exercise vital sign detection radar is provided, including a transmitting unit, a receiving unit, and a signal processing module. The transmitting unit is configured to transmit an incident radar signal. The receiving unit is configured to receive a reflected radar signal. The signal processing module is configured to obtain a corresponding digital signal according to the reflected radar signal, obtain a phase map and a vibration frequency map according to the digital signal, select at least one candidate position from the vibration frequency map, select a target position from the at least one candidate position, obtain one or more pieces of target phase data in a distance range in the phase map according to the target position, and input the one or more pieces of target phase data into a machine learning model to obtain a vital sign parameter prediction result. The phase map presents an energy distribution with a distance change relative to the exercise vital sign detection radar and a phase change. The vibration frequency map presents an energy distribution with the distance change relative to the exercise vital sign detection radar and a vibration frequency change. The target position is a position having a vibration frequency meeting a vital sign parameter range in the at least one candidate position.

According to some embodiments, the target position is a position that has a vibration frequency meeting a vital sign parameter range in the at least one candidate position and has the highest energy intensity.

According to some embodiments, the energy threshold for each range bin in the phase map is calculated, and energy values of phases on the each range bin are separately compared with the energy threshold corresponding to the range bin, to select the at least one candidate position having an energy intensity exceeding the energy threshold.

According to some embodiments, the energy threshold is determined according to an average energy value or a maximum energy value of the corresponding range bin.

According to some embodiments, the energy threshold is a sum of a times the average energy value and b times the maximum energy value, $a+b=1$, and a and b are positive numbers.

According to some embodiments, the energy threshold is a times the average energy value, and a is a positive number.

According to some embodiments, the vibration frequency map is obtained by performing Fast Fourier Transform (FFT) on phase distributions on ranges on the phase map.

According to some embodiments, FFT is performed on the digital signal to obtain a range profile map, where the range profile map presents an energy distribution with the distance change relative to the exercise vital sign detection radar and a time change.

According to some embodiments, phase unwrapping is performed on the range profile map to obtain the phase map.

According to some embodiments, the one or more pieces of target phase data are a plurality of range bins in the phase map, and one of the pieces of target phase data includes the target position.

According to some embodiments, N to-be-detected target positions are selected from the at least one candidate position, where N is greater than 1, and the N to-be-detected target positions are positions that have the vibration frequency meeting the vital sign parameter range in the at least one candidate position and have top N energy intensities; one or more pieces of to-be-detected target phase data in a corresponding distance range in the phase map are obtained according to each of the to-be-detected target positions; and the one or more pieces of to-be-detected target phase data of the each to-be-detected target position are inputted into the machine learning model, to obtain a vital sign parameter prediction result corresponding to the each to-be-detected target position.

Based on the above, through the non-contact exercise vital sign detection method and the exercise vital sign detection radar according to some embodiments, vital sign parameters can be accurately detected in a non-contact manner when a subject is in an exercise state.

DETAILED DESCRIPTION

A term "connect" used in this specification means that two or more elements are in physical or electrical contact with each other directly, or are in physical or electrical contact with each other indirectly.

Figure 1:
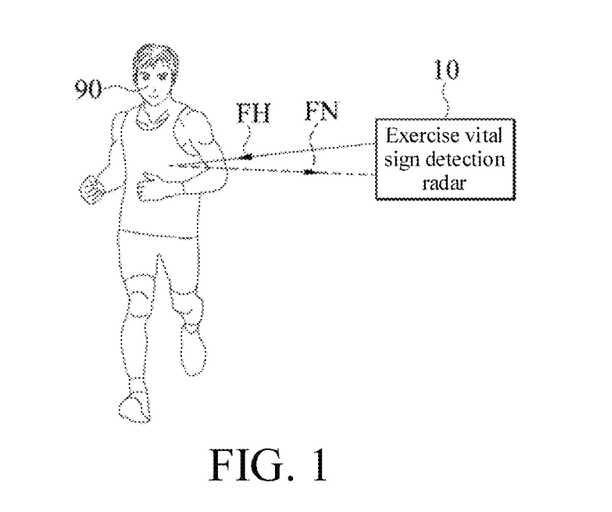
FIG. 1 is a schematic diagram of a use state of an exercise vital sign detection radar according to some embodiments.

FIG. 1 is a schematic diagram of a use state of an exercise vital sign detection radar 10 according to some embodiments. The exercise vital sign detection radar 10 transmits a radar signal (hereinafter referred to as "incident radar signal FH"). The incident radar signal FH is transmitted to a target 90, modulated due to the exercise of the target 90 (for example, a subject), and reflected to the exercise vital sign detection radar 10. The radar signal that is reflected is referred to as "reflected radar signal FN" hereinafter. Therefore, one or more types of information of the target 90 can be detected by analyzing the reflected radar signal FN. The information may be, for example, speed, distance, orientation, vital sign information (such as heartbeat, or respiration), and the like.

In some embodiments, the exercise vital sign detection radar 10 may be an FMCW radar, a continuous wave (CW) radar, or an ultra-wideband (UWB) radar. Descriptions are made below by using an FMCW radar as an example.

Figure 2:
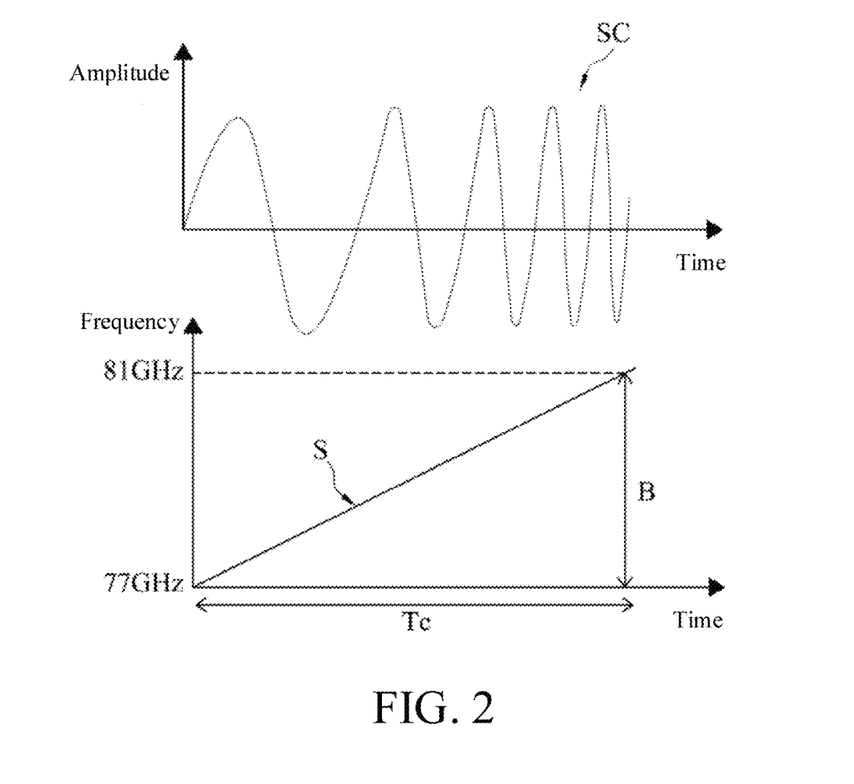
FIG. 2 is a schematic diagram of illustrating a radar signal.

FIG. 2 is a schematic diagram of illustrating a radar signal. An upper half shows a change of an amplitude of the incident radar signal FH with time, and a lower half shows a change of a frequency of the incident radar signal FH with time. The incident radar signal FH includes a plurality of chirped pulses SC. FIG. 2 shows only one chirped pulse SC for clarity. The chirped pulse SC is a linear frequency modulation pulse signal, which refers to a sine wave with a frequency increasing in a linear manner with time. In some embodiments, a frequency of the chirped pulse SC increases in a nonlinear manner. For ease of description, descriptions are made below by using a linear manner. As shown in FIG. 2, within a duration Tc (for example, 40 microseconds), the chirped pulse SC linearly increases from a start frequency (for example, 77 GHz) to a stop frequency (for example, 81 GHz) according to a slope S. The start frequency and the stop frequency may be selected from a millimeter wave frequency band (namely, 30 GHz to 300 GHz). A difference between the start frequency and the stop frequency is a pulse bandwidth B.

Figure 3:
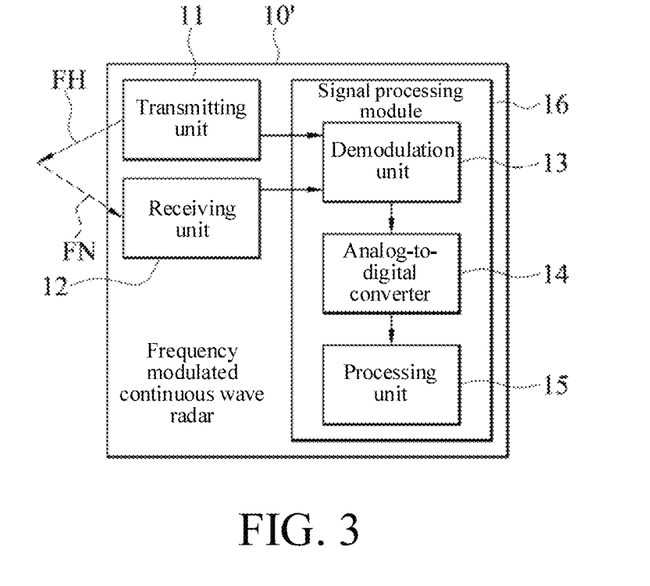
FIG. 3 is a schematic block diagram of a frequency modulated continuous wave (FMCW) radar according to some embodiments.
Figure 4:
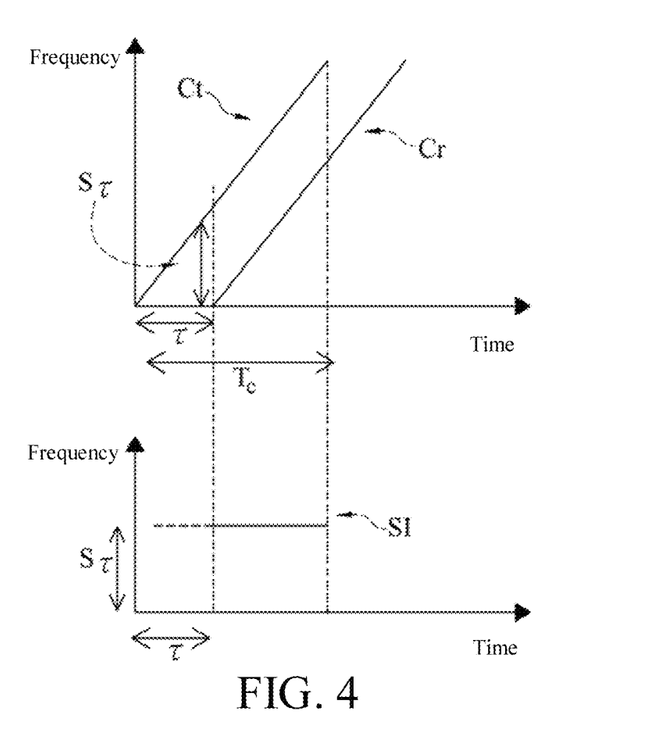
FIG. 4 is a schematic diagram of illustrating an incident radar signal and a reflected radar signal.
Figure 5:
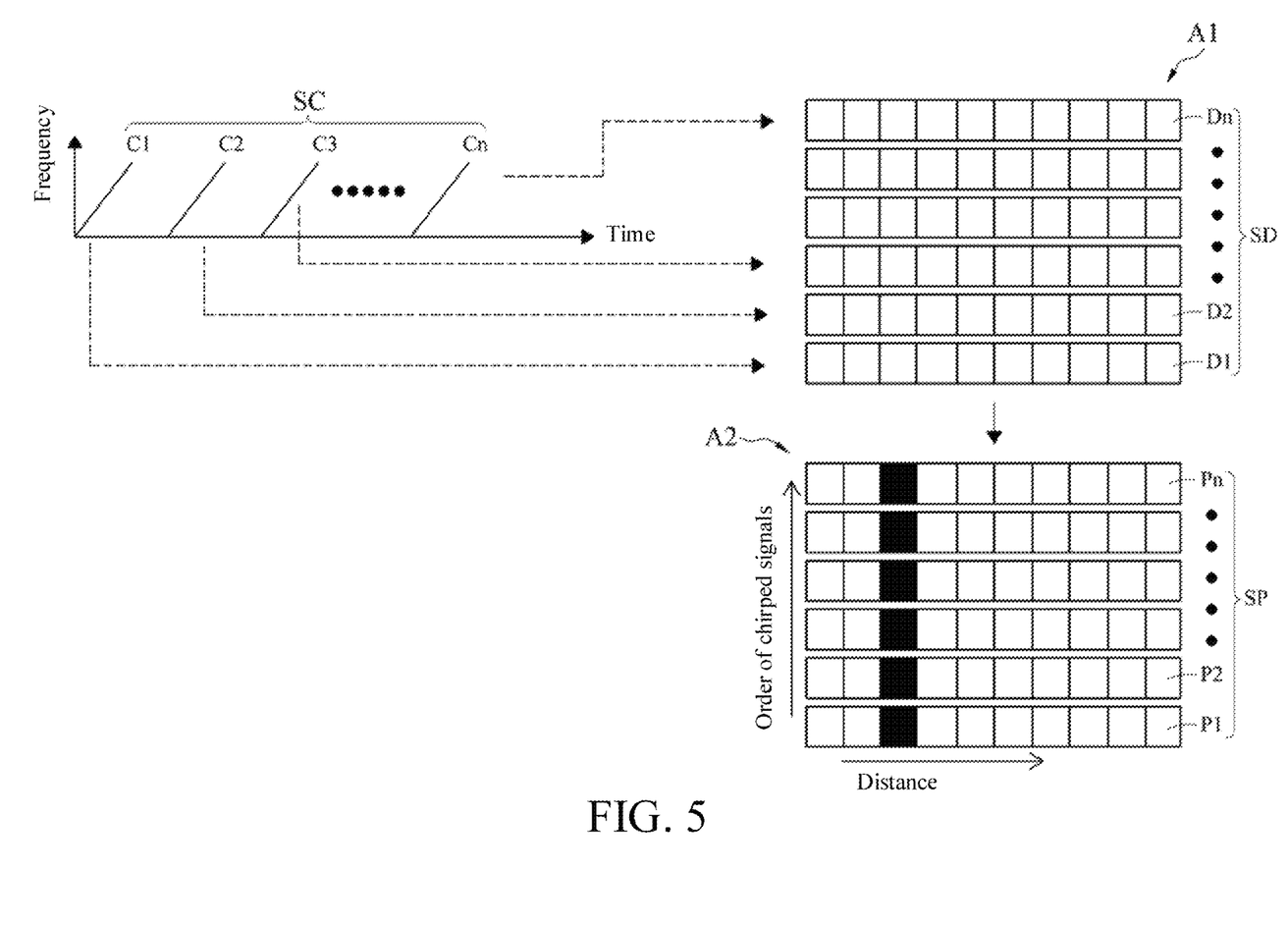
FIG. 5 is a schematic diagram of signal processing according to some embodiments.

Refer to FIG. 3 and FIG. 4 together. FIG. 3 is a schematic block diagram of an FMCW radar 10' according to some embodiments. FIG. 4 is a schematic diagram of illustrating an incident radar signal FH and a reflected radar signal FN. The FMCW radar 10' includes a transmitting unit 11, a receiving unit 12, a demodulation unit 13, an analog-to-digital converter 14, and a processing unit 15. The transmitting unit 11 is configured to transmit the incident radar signal FH, and includes a transmitting antenna and a signal synthesizer. The signal synthesizer is configured to generate the incident radar signal FH including a chirped pulse Ct, and the incident radar signal FH is transmitted by using the transmitting antenna. The receiving unit 12 includes a receiving antenna configured to receive the reflected radar signal FN including at least one chirped pulse Cr. The chirped pulse Cr may be regarded as a delayed chirped pulse Ct. The demodulation unit 13, the analog-to-digital converter 14, and the processing unit 15 are configured to process the received reflected radar signal FN, and may be collectively referred to as a signal processing module 16. The demodulation unit 13 is connected to the transmitting unit 11 and the receiving unit 12, and includes a mixer and a low-pass filter. The mixer couples the chirped pulse Ct of the incident radar signal FH and the chirped pulse Cr corresponding to the reflected radar signal FN, which can generate two coupled signals such as a sum of a frequency of the chirped pulse Ct and a frequency of the chirped pulse Cr, and a difference between the frequency of the chirped pulse Ct and the frequency of the chirped pulse Cr. The low-pass filter performs low-pass filtering on the coupled signals to remove a high-frequency component to obtain the coupled signal of the difference between the frequency of the chirped pulse Ct and the frequency of the chirped pulse Cr, which is hereinafter referred to as "intermediate frequency signal SI". The analog-to-digital converter 14 connects between the demodulation unit 13 and the processing unit 15. The analog-to-digital converter 14 converts the intermediate frequency signal SI into a digital signal SD (as shown in FIG. 5). The processing unit 15 performs digital signal processing on the digital signal SD. The processing unit 15 may be, for example, a central processing unit (CPU), a graphics processing unit (GPU), or a microprocessor, a digital signal processor (DSP), a programmable controller, an application-specific integrated circuit (ASIC), or a programmable logic device (PLD) with general purposes or special purposes, or other similar apparatuses, chips, integrated circuits, or a combination thereof.

Figure 15:
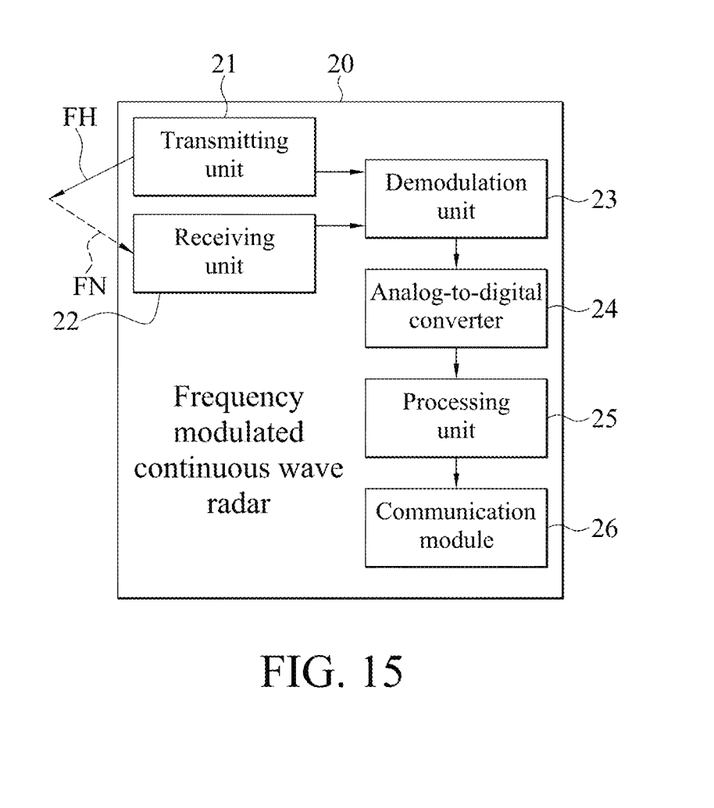
FIG. 15 is a schematic block diagram of an FMCW radar according to some embodiments.

Refer to FIG. 15. FIG. 15 is a schematic block diagram of an FMCW radar 20 according to some embodiments. FMCW radar 20 includes a transmitting unit 21, a receiving unit 22, a demodulation unit 23, an analog-to-digital converter 24, a processing unit 25, and a communication module 26. The transmitting unit 21, the receiving unit 22, the demodulation unit 23, the analog-to-digital converter 24 and the processing unit 25 are the same as the transmitting unit 11, the receiving unit 12, the demodulation unit 13, the analog-to-digital converter 14 and the processing unit 15, and therefore the descriptions are not repeated. The the communication module 26 connects to the processing unit 25. In an embodiment, the communication module 26 transmits the digital signal SD outputting from the analog-to-digital converter 24 to another device or a cloud server for further processing. In some another embodiment, the processing unit 25 processes some of the digital signals SD from the analog-to-digital converter 24, and processing results of some of the digital signals are transmitted to the another device or the cloud server through the communication module 26 for further processing. The communication module 26 may be, for example, a wired communication interface such as Universal Asynchronous Receiver Transmitter (UART)/Integrated Circuit Bus (I²C)/Serial Peripheral Interface (SPI)/Controller Area Network (CAN)/Recommended Standard (RS) 232/Recommended Standard (RS) 422, etc. The communication module 26 may be, for example, but not limited to, a wireless communication interface such as a wireless sensor network (eg, EnOcean/Bluetooth/ZigBee), a cellular network (2G/3G/Long Term Evolution (LTE)/5G), Wireless Local Area Network (for example, Wireless Local Area Network (WLAN)/World Interoperability for Microwave Connectivity (WiMAX)), short-range point-to-point communication (for example, Radio Frequency Identification (RFID)/EnOcean/Near Field Communication (NFC)), etc.

Referring to FIG. 4, a frequency $f_0$ of the intermediate frequency signal SI may be expressed as Equation 1, where S is a slope, and $\tau$ is a delay time between transmitting the incident radar signal FH and receiving the reflected radar signal FN. Therefore, $\tau$ may be expressed as Equation 2, where d is a distance between the transmitting antenna of the radar and the target 90, and c is the speed of light. Equation (3) can be obtained by substituting Equation (2) into Equation (1). It can be known from Equation 3 that the frequency $f_0$ of the intermediate frequency signal SI implies distance information (that is, a distance between the FMCW radar 10' and the target 90).

$$f_0 = S \cdot \tau \qquad \text{Equation 1}$$

$$\tau = 2d/c \qquad \text{Equation 2}$$

$$f_0 = 2Sd/c \qquad \text{Equation 3}$$

FIG. 5 is a schematic diagram of signal processing according to some embodiments. Chirped pulses SC are respectively numbered as C1, C2, C3, . . . , and Cn in sequence, where n is a positive integer. The analog-to-digital converter 14 converts received intermediate frequency signals SI corresponding to the chirped pulses C1 to Cn into digital signals SD (which are respectively expressed as sequences D1, D2, . . . , and Dn, n being a positive integer), and each chirped pulse Cx (x=1 to n) corresponds to a sequence Dx (x=1 to n). Each sequence Dx (x=1 to n) of the digital signals SD may be expressed as a one-dimensional array (a row matrix). The transverse arrays Dx (x=1 to n) are arranged longitudinally in sequence to form a two-dimensional matrix A1. It can be understood that the digital signals SD may alternatively be arranged to form column arrays, and the column arrays are arranged transversely in sequence. Similarly, another two-dimensional matrix can be obtained. Values of the two-dimensional matrix A1 represent signal strengths (amplitudes). An index value x of a column of the two-dimensional matrix A1 corresponds to an order of the chirped pulses SC. An index value of a row of the two-dimensional matrix A1 has the meaning of time. That is, the row array of the two-dimensional matrix A1 is a time-domain signal (a set of digital data related to time).

The processing unit 15 performs FFT (which is hereinafter referred to as "distance Fourier transform") on the row arrays of the two-dimensional matrix A1 (that is, the two-dimensional matrix A1 formed by the digital signals SD) to obtain frequency-domain signals SP (which are respectively expressed as P1, P2, . . . , and Pn, n being a positive integer), that is, the two-dimensional matrix A2. Therefore, the row arrays of the two-dimensional matrix A2 are equivalent to a frequency spectrum distribution in response to a chirped pulse Cx. As described above, the frequency of the intermediate frequency signal SI implies distance information. That is, an index value of a row of the two-dimensional matrix A2 has the meaning of distance. Values of the two-dimensional matrix A2 represent intensities of frequencies on a frequency spectrum, which can present strengths of radar signals reflected at different distances from the FMCW radar 10'. As shown in FIG. 5, a colored box in the two-dimensional matrix A2 is a peak (that is, a value exceeds a threshold), which indicates that there is a target 90 at a distance corresponding to the frequency. A distance between the FMCW radar 10' and the target 90 can be calculated according to the frequency at the peak. Further, wide-range exercise information (such as an average speed) can be obtained through calculation according to specific distance changes of the target 90 calculated at different time points.

Descriptions are made above by using an example in which the transmitting unit 11 has one transmitting antenna and the receiving unit 12 has one receiving antenna. However, in some embodiments, the transmitting unit 11 has a plurality of transmitting antennas to transmit a plurality of incident radar signals FH. Similarly, in some embodiments, the receiving unit 12 has a plurality of receiving antennas.

Figure 6:
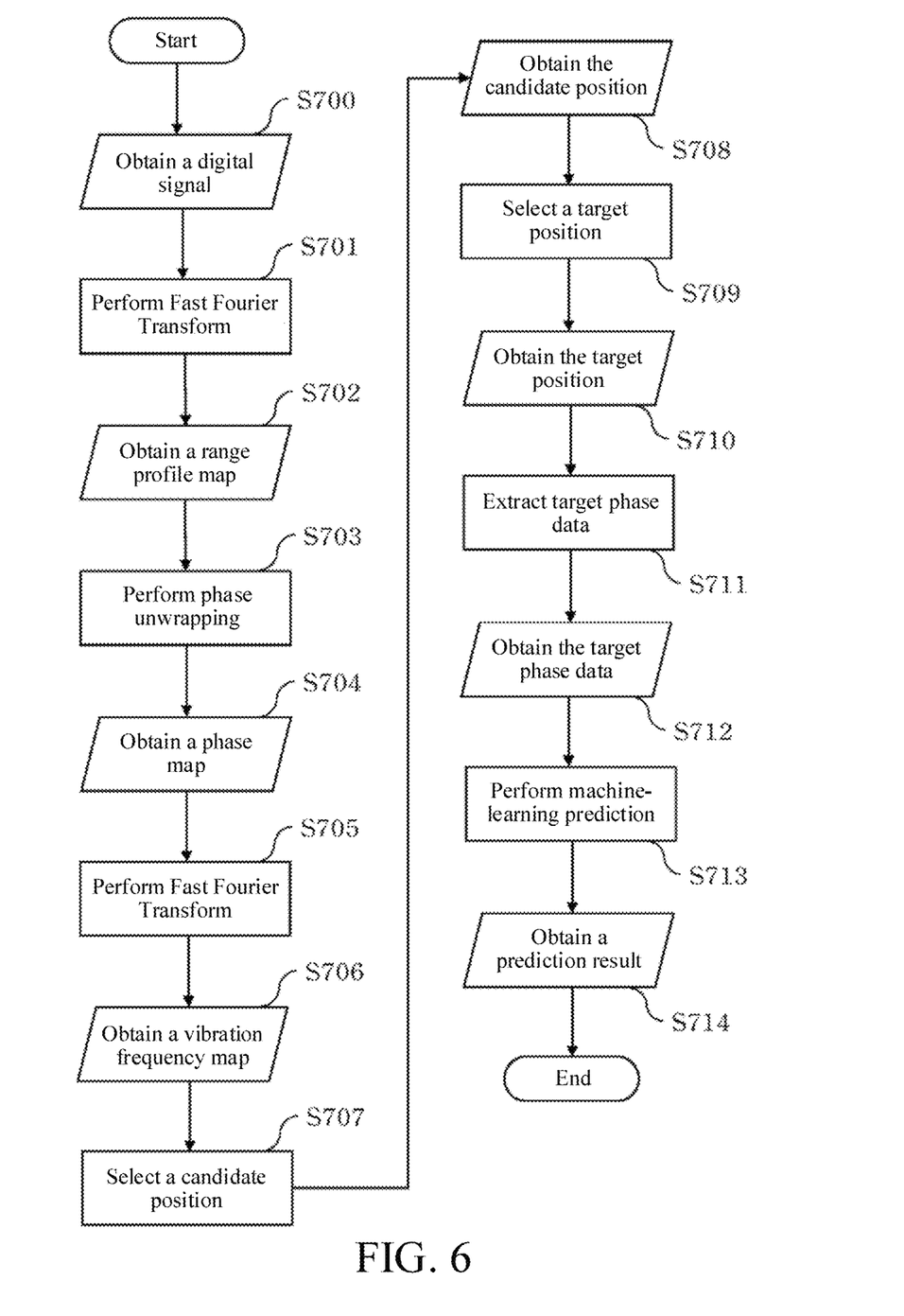
FIG. 6 is a flowchart of a non-contact exercise vital sign detection method according to some embodiments.
Figure 7:
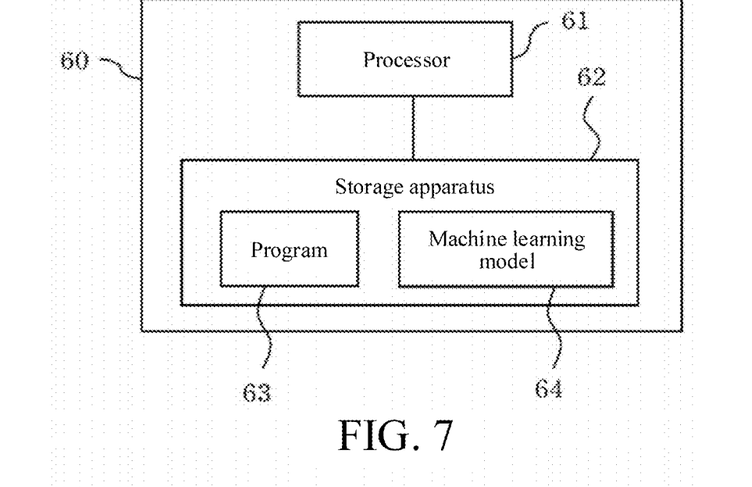
FIG. 7 is a schematic block diagram of a signal processing apparatus according to some embodiments.

Refer to FIG. 6 and FIG. 7 together. FIG. 6 is a flowchart of a non-contact exercise vital sign detection method according to some embodiments. FIG. 7 is a schematic block diagram of a signal processing apparatus 60 according to some embodiments. The signal processing apparatus 60 includes a processor 61 and a storage apparatus 62. The storage apparatus 62 is a computer-readable storage medium for storing a program 63 executed by the processor 61 to perform the non-contact exercise vital sign detection method. In some embodiments, the signal processing apparatus 60 is the foregoing FMCW radar 10', and the processor 61 is the foregoing processing unit 15. In some embodiments, the signal processing apparatus 60 is an edge apparatus or a cloud server. That is, after obtaining the digital signal SD, the FMCW radar 10' transmits the digital signal SD to the edge apparatus or the cloud server, and the edge apparatus or the cloud server performs digital signal processing on the digital signal SD.

Figure 8:
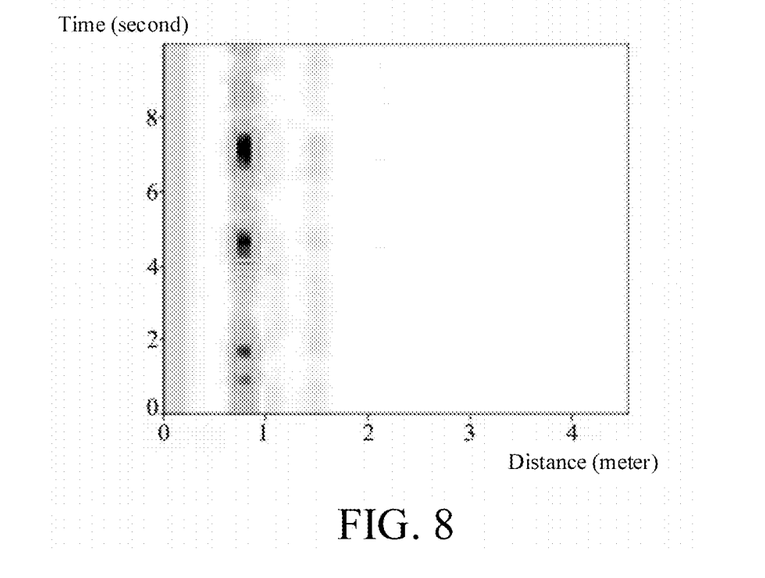
FIG. 8 is a schematic diagram of a range profile map according to some embodiments.

As described above, the analog-to-digital converter 14 may convert the received intermediate frequency signals SI corresponding to the chirped pulses Cx into the digital signals SD, and therefore, the processor 61 can obtain a digital signal SD corresponding to the reflected radar signal FN (step S700). Subsequently, a range profile map can be obtained (step S702) according to the foregoing distance Fourier transform (step S701). FIG. 8 is a schematic diagram of a range profile map according to some embodiments. The range profile map presents an energy distribution with a distance change (transverse axis) and a time change (longitudinal axis) relative to the FMCW radar 10', and an energy difference is presented by color depth herein.

Figure 9:
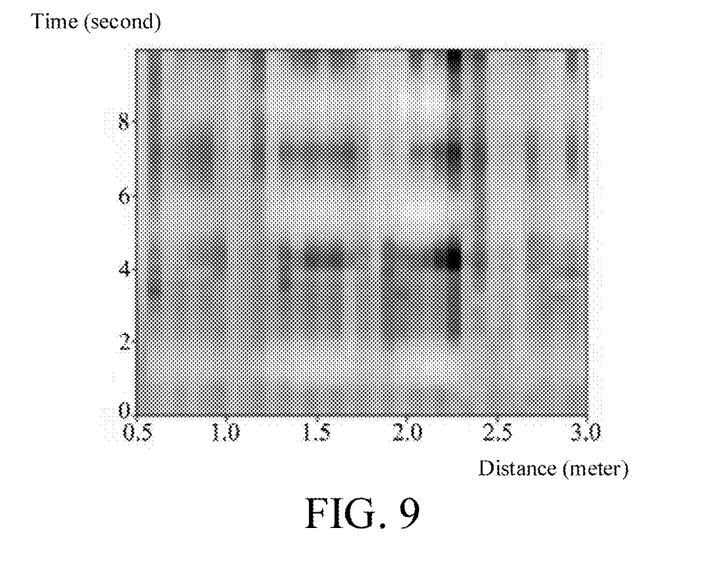
FIG. 9 is a schematic diagram of a phase map according to some embodiments.
Figure 10:
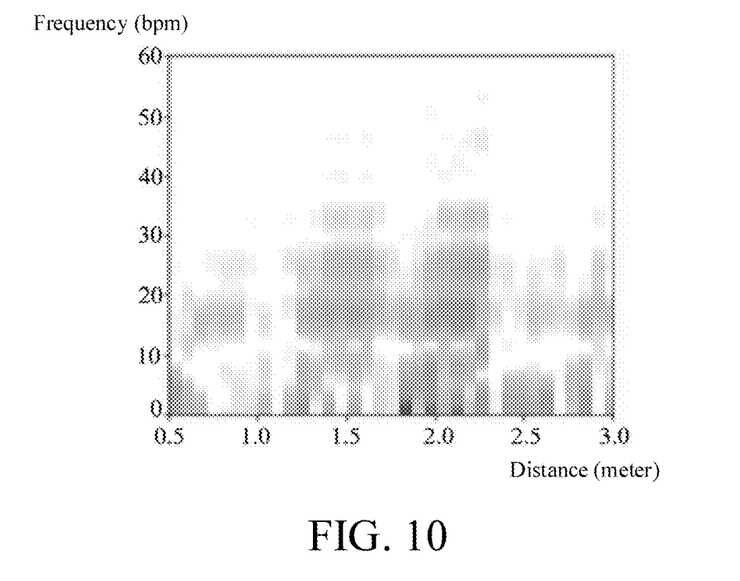
FIG. 10 is a schematic diagram of a vibration frequency map according to some embodiments.

According to the digital signal SD, in addition to the range profile map, a phase map and a vibration frequency map can be further obtained. In step S703, phase unwrapping is performed on the range profile map to obtain a phase map (step S704). FIG. 9 is a schematic diagram of a phase map according to some embodiments. The phase map presents an energy distribution with a distance change (transverse axis) and a phase change (longitudinal axis) relative to the FMCW radar 10', and an energy difference is presented by color depth herein. Subsequently, in step S705, FFT is performed on phase distributions (that is, range bins) on ranges on the phase map to obtain a vibration frequency map (step S706). FIG. 10 is a schematic diagram of a vibration frequency map according to some embodiments. The vibration frequency map presents an energy distribution with a distance change (transverse axis) and a vibration frequency change (longitudinal axis) relative to the FMCW radar 10', and an energy difference is presented by color depth herein.

Figure 11:
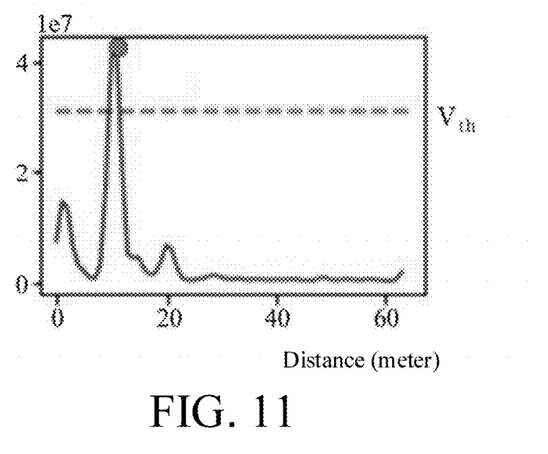
FIG. 11 is a schematic diagram of a vibration frequency distribution of range bins according to some embodiments.

After the vibration frequency map is obtained, in step S707, at least one candidate position having an energy intensity exceeding an energy threshold $V_{th}$ is selected from the vibration frequency map (step S708). FIG. 11 is a schematic diagram of a vibration frequency distribution of range bins according to some embodiments. FIG. 11 presents a peak exceeding the energy threshold $V_{th}$, and therefore, the range bin is selected as a candidate position. In other words, in step S707, each range bin in the phase map is compared with the energy threshold $V_{th}$. If the energy threshold $V_{th}$ is exceeded, the corresponding range bin is selected as a candidate position.

In some embodiments, the energy threshold $V_{th}$ is a floating threshold. The energy threshold $V_{th}$ is calculated for each range bin in the phase map. The energy threshold $V_{th}$ is determined according to an average energy value or a maximum energy value of the corresponding range bin. For example, the energy threshold is a sum of a times the average energy value and b times the maximum energy value, a+b=1, and a and b are positive numbers. In another example, the energy threshold is a times the average energy value, and a is a positive number.

There may be a plurality of candidate positions obtained in the foregoing step S708. Therefore, it is necessary to further determine which one should be selected to eliminate interference signals. In step S709, one or more candidate positions are selected from the candidate positions to obtain one or more target positions (step S710). The target position is a position having a vibration frequency meeting a vital sign parameter range in the candidate positions. The vital sign parameter range may be, for example, a respiratory rate range (such as 10 to 20 breaths per minute), or a heart rate range (such as 60 to 100 beats per minute (bpm)).

Specifically, in some embodiments, there is one target 90 in a detection field. Candidate positions having the vibration frequency meeting the vital sign parameter range are found out, and one of the candidate positions that has the highest energy intensity in a vibration frequency range is selected. The selected candidate position (distance) is a position (that is, the target position) of the target 90.

In some embodiments, there are a plurality of targets 90 in the detection field. N to-be-detected target positions are selected from the candidate positions, where N is greater than 1. The N to-be-detected target positions are positions that have the vibration frequency meeting the vital sign parameter range in the candidate positions and have top N energy intensities. The to-be-detected target positions are positions (that is, the target positions) of the targets 90.

After one or positions of one or more targets are determined, corresponding one or more pieces of target phase data (or referred to as to-be-detected target phase data) can be extracted accordingly (step S711). It is taken into consideration that a misjudgment may be generated during detection of an object in an exercise state to cause a deviation. In step S711, a piece of target phase data in a corresponding distance range in the phase map is obtained according to each target position (step S712). In some embodiments, one piece of target phase data in a corresponding distance range in the phase map is obtained according to each target position. The target phase data includes a range bin of the target position. In some other embodiments, a plurality of pieces of target phase data in a corresponding distance range in the phase map are obtained according to each target position. The pieces of target phase data further include one or more range bins adjacent to the target position in addition to a range bin of the target position. For example, two range bins on either side are taken by using the range bin of the target position as a center, and the target phase data includes five range bins.

In step S713, the target phase data of the each to-be-detected target position is inputted into a machine learning model 64, to obtain a vital sign parameter prediction result (step S714). For example, a corresponding respiratory rate or heart rate is predicted. In some embodiments, the target phase data is normalized and then inputted into the machine learning model 64.

In an embodiment, the machine learning model 64 is a MobileNetV3 model.

Figure 12:
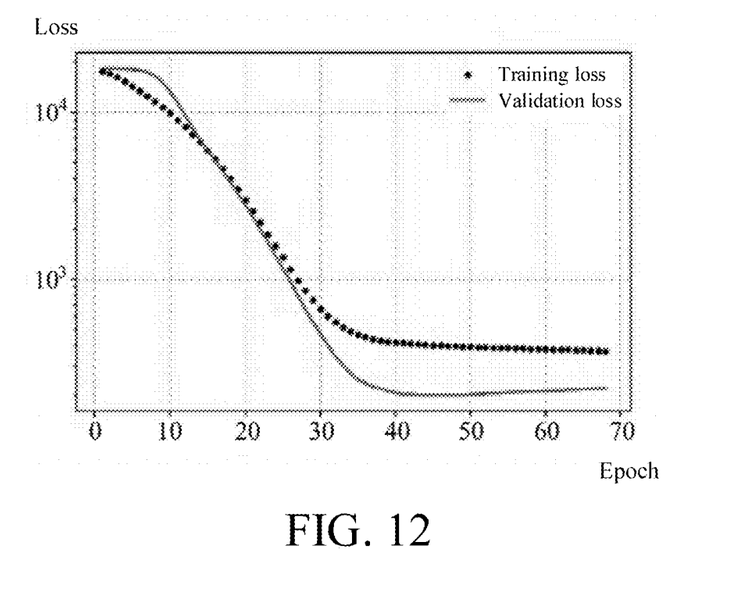
FIG. 12 is a diagram of loss-epoch changes of a machine learning model on a training set and a validation set according to some embodiments.
Figure 13:
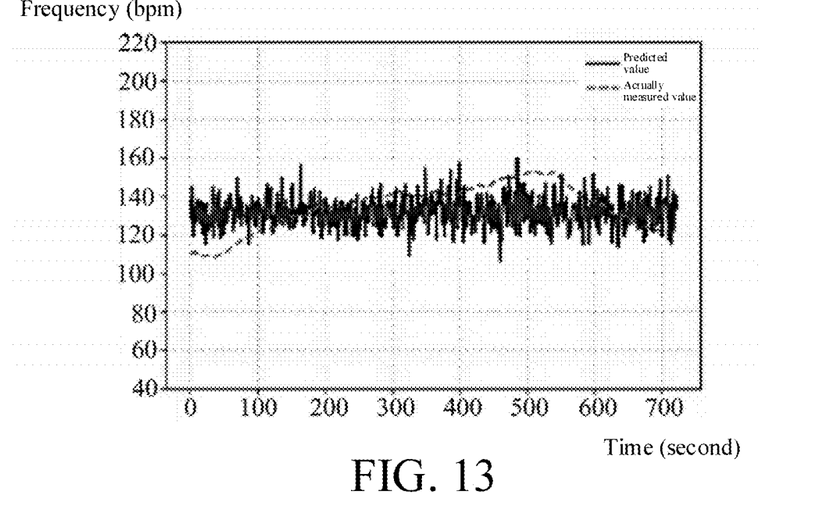
FIG. 13 is a schematic diagram of a vital sign parameter prediction result according to some embodiments.
Figure 14:
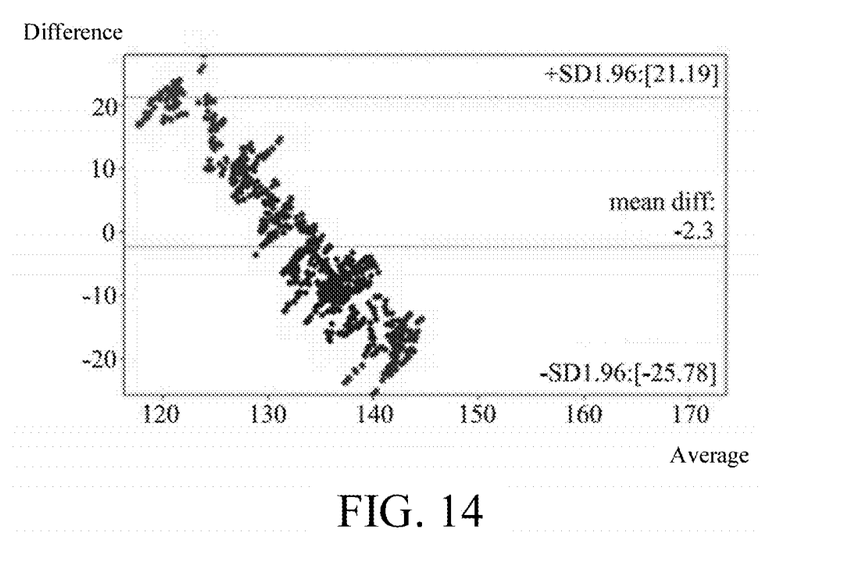
FIG. 14 is a Bland-Altman plot according to some embodiments.

Training samples are acquired usage data of three types of sports equipment (bicycle, elliptical machine, and treadmill). 30 person-pieces of radar data are collected for each type of sports equipment, and there are a total of 90 person-pieces of radar data. Each piece of radar data includes data of four exercise intensities (at rest, slow, moderate, and fast), and each exercise intensity lasts for two minutes. The FMCW radar 10' is mounted at a height of 1.6 to 2 meters and at a distance of 0.7 to 0.9 meters from a subject. During collection, the subject wears a cardiotachometer to obtain a real-time heart rate synchronously as a labeled sample. FIG. 12 is a diagram of loss-epoch changes of the machine learning model 64 on a training set and a validation set according to some embodiments. It can be learned that the model is converged well. There are a total of 7047 pieces of training data, a learning rate is $10^{-5}$, a training loss is 397.11, and a test loss is 201.52. FIG. 13 is a schematic diagram of a vital sign parameter prediction result according to some embodiments. An accuracy rate is 91.23%, a root-mean-square error is 14.2 (bpm), and a standard error is 8.15 (bpm). FIG. 14 is a Bland-Altman plot according to some embodiments, to determine, through comparison, the consistency between a predicted heart rate and an actual value measured by using a cardiotachometer. A quantity of sampling is 723. A maximum deviation is 27.84, a minimum deviation is −25.69, an average deviation is −2.3, a standard deviation is 11.98, and a 95% confidence interval of a regression line is [−27.78, 21.19]. It can be learned that the predicted heart rate is close to the actual value measured by using the cardiotachometer.

In the foregoing non-contact exercise vital sign detection method, the digital signal SD is obtained in a sliding window manner and processed. In some embodiments, a size of a window is 10 seconds, and a time step is one second.

Based on the above, through the non-contact exercise vital sign detection method and the exercise vital sign detection radar 10 according to some embodiments, vital sign parameters can be accurately detected in a non-contact manner when a subject is in an exercise state.

What is claimed is:

1. A non-contact exercise vital sign detection method, performed by a processor in a signal processing apparatus, the method comprising:
    obtaining a digital signal;
    obtaining a phase map and a vibration frequency map according to the digital signal, wherein the phase map presents an energy distribution with a distance change relative to an exercise vital sign detection radar and a phase change, and the vibration frequency map presents an energy distribution with the distance change relative to the exercise vital sign detection radar and a vibration frequency change;
    selecting at least one candidate position having an energy intensity exceeding an energy threshold from the vibration frequency map;
    selecting a target position from the at least one candidate position, wherein the target position is a position having a vibration frequency meeting a vital sign parameter range in the at least one candidate position;
    obtaining one or more pieces of target phase data in a distance range in the phase map according to the target position; and
    inputting the one or more pieces of target phase data into a machine learning model to obtain a vital sign parameter prediction result.

2. The non-contact exercise vital sign detection method according to claim 1, wherein the digital signal corresponds to a reflected radar signal of the exercise vital sign detection radar; and
    the target position is a position that has the vibration frequency meeting the vital sign parameter range in the at least one candidate position and has the highest energy intensity.

3. The non-contact exercise vital sign detection method according to claim 2, wherein the step of selecting the at least one candidate position from the vibration frequency map comprises:
    calculating the energy threshold for each range bin in the phase map; and
    separately comparing energy values of phases on the each range bin with the energy threshold corresponding to the range bin, to select the at least one candidate position having an energy intensity exceeding the energy threshold from the vibration frequency map.

4. The non-contact exercise vital sign detection method according to claim 3, wherein the energy threshold is determined according to an average energy value or a maximum energy value of the corresponding range bin.

5. The non-contact exercise vital sign detection method according to claim 4, wherein the energy threshold is a sum of a times the average energy value and b times the maximum energy value, a+b=1, and a and b are positive numbers.

6. The non-contact exercise vital sign detection method according to claim 4, wherein the energy threshold is a times the average energy value, and a is a positive number.

7. The non-contact exercise vital sign detection method according to claim 1, wherein the vibration frequency map is obtained by performing Fast Fourier Transform (FFT) on phase distributions on ranges on the phase map.

8. The non-contact exercise vital sign detection method according to claim 1, wherein the step of obtaining the phase map comprises:
    performing FFT on the digital signal to obtain a range profile map, wherein the range profile map presents an energy distribution with the distance change relative to the exercise vital sign detection radar and a time change.

9. The non-contact exercise vital sign detection method according to claim 8, wherein the step of obtaining the phase map further comprises:
    performing phase unwrapping on the range profile map to obtain the phase map.

10. The non-contact exercise vital sign detection method according to claim 1, wherein the one or more pieces of target phase data are a plurality of range bins in the phase map, and one of the pieces of target phase data comprises the target position.

11. The non-contact exercise vital sign detection method according to claim 1, further comprising:
    selecting N to-be-detected target positions from the at least one candidate position, wherein N is greater than 1, and the N to-be-detected target positions are positions that have the vibration frequency meeting the vital sign parameter range in the at least one candidate position and have top N energy intensities;
    obtaining one or more pieces of to-be-detected target phase data in a corresponding distance range in the phase map according to each of the to-be-detected target positions; and
    inputting the one or more pieces of to-be-detected target phase data of the each to-be-detected target position into the machine learning model, to obtain a vital sign parameter prediction result corresponding to the each to-be-detected target position.

12. An exercise vital sign detection radar, comprising:
    a transmitting unit, configured to transmit an incident radar signal;
    a receiving unit, configured to receive a reflected radar signal; and
    a signal processing module, configured to obtain a corresponding digital signal according to the reflected radar signal, obtain a phase map and a vibration frequency map according to the digital signal, select at least one candidate position from the vibration frequency map, select a target position from the at least one candidate position, obtain one or more pieces of target phase data in a distance range in the phase map according to the target position, and input the one or more pieces of target phase data into a machine learning model to obtain a vital sign parameter prediction result,
    wherein the phase map presents an energy distribution with a distance change relative to the exercise vital sign detection radar and a phase change, the vibration frequency map presents an energy distribution with the distance change relative to the exercise vital sign detection radar and a vibration frequency change, and the target position is a position having a vibration frequency meeting a vital sign parameter range in the at least one candidate position.

13. The exercise vital sign detection radar according to claim 12 wherein the target position is a position that has a vibration frequency meeting a vital sign parameter range in the at least one candidate position and has the highest energy intensity.

14. The exercise vital sign detection radar according to claim 13, wherein the signal processing module calculates an energy threshold for each range bin in the phase map, and separately compares energy values of phases on the each range bin with the energy threshold corresponding to the range bin, to select the at least one candidate position having an energy intensity exceeding the energy threshold from the vibration frequency map.

15. The exercise vital sign detection radar according to claim 14, wherein the energy threshold is determined according to an average energy value or a maximum energy value of the corresponding range bin.

16. The exercise vital sign detection radar according to claim 15, wherein the energy threshold is a sum of a times the average energy value and b times the maximum energy value, a+b=1, and a and b are positive numbers.

17. The exercise vital sign detection radar according to claim 15, wherein the energy threshold is a times the average energy value, and a is a positive number.

18. The exercise vital sign detection radar according to claim 12, wherein the vibration frequency map is obtained by performing Fast Fourier Transform (FFT) on phase distributions on ranges on the phase map.

19. The exercise vital sign detection radar according to claim 12, wherein the signal processing module performs FFT on the digital signal to obtain a range profile map, and the range profile map presents an energy distribution with the distance change relative to the exercise vital sign detection radar and a time change.

20. The exercise vital sign detection radar according to claim 19, wherein the signal processing module performs phase unwrapping on the range profile map to obtain the phase map.

21. The exercise vital sign detection radar according to claim 12, wherein the one or more pieces of target phase data are a plurality of range bins in the phase map, and one of the pieces of target phase data comprises the target position.

22. The exercise vital sign detection radar according to claim 12, wherein
the signal processing module selects N to-be-detected target positions from the at least one candidate position, wherein N is greater than 1, and the N to-be-detected target positions are positions that have the vibration frequency meeting the vital sign parameter range in the at least one candidate position and have top N energy intensities;
the signal processing module obtains one or more pieces of to-be-detected target phase data in a corresponding distance range in the phase map according to each of the to-be-detected target positions; and
the signal processing module inputs the one or more pieces of to-be-detected target phase data of the each to-be-detected target position into the machine learning model, to obtain a vital sign parameter prediction result corresponding to the each to-be-detected target position.

* * * * *